United States Patent [19]
McAtee et al.

[11] Patent Number: 5,942,238
[45] Date of Patent: *Aug. 24, 1999

[54] METHOD FOR REMOVING MAKE-UP FROM SKIN

[75] Inventors: David Michael McAtee, Mason; Robert Bao Kim Ha, Milford; Lourdes Dessus Albacarys, West Chester, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/789,357

[22] Filed: Jan. 27, 1997

[51] Int. Cl.⁶ .................. A61K 6/00; A61K 7/00
[52] U.S. Cl. ........................ 424/401; 424/78.03
[58] Field of Search ............... 424/70.24, 401, 424/70.25, 402, 70.22, 403, 78.03, 404; 252/91; 514/865, 938, 939

[56] References Cited

U.S. PATENT DOCUMENTS

| 3,795,624 | 3/1974 | Feinstone | 252/91 |
| 5,372,744 | 12/1994 | Kamegai | 252/174.17 |
| 5,409,640 | 4/1995 | Giret et al. | 252/546 |
| 5,439,682 | 8/1995 | Wivell et al. | 724/401 |
| 5,648,083 | 7/1997 | Blieszner et al. | 424/402 |

FOREIGN PATENT DOCUMENTS

| 0 541 347 A2 | 5/1993 | European Pat. Off. | A61K 7/02 |
| 678269 A5 | 8/1991 | Switzerland | A61K 7/02 |
| 2 280 682 | 2/1985 | United Kingdom | C11D 17/00 |
| 92/06160 | 4/1992 | WIPO | C11D 1/835 |
| 92/18100 | 10/1992 | WIPO | A61K 7/50 |

OTHER PUBLICATIONS

Patent Abstracts of Japan, vol. 095, No. 011, Dec. 26, 1995 (JP 07 223923A).

*Primary Examiner*—Thurman K. Page
*Assistant Examiner*—S. Howard
*Attorney, Agent, or Firm*—Stephen T. Murphy; Armina E. Matthews; George W. Allen

[57] ABSTRACT

The present invention relates to a method for removing make-up from human skin comprising applying a cleansing composition comprising a lathering surfactant and water, wherein the pH of the composition is less than about 8.3 and wherein the interfacial tension of the composition with mineral oil is less than about 3.5.

7 Claims, No Drawings

METHOD FOR REMOVING MAKE-UP FROM SKIN

TECHNICAL FIELD

The present invention relates to methods for cleansing the face and for removing make-up from the face using personal cleansing using surfactant solutions which have low pH and low interfacial tension. These solutions provide properties better matched for removing silicone based make-ups.

BACKGROUND OF THE INVENTION

Personal cleansing products have traditionally been marketed in a variety of forms such as bar soaps, creams, lotions, and gels. These cleansing formulations have attempted to satisfy a number of criteria to be acceptable to consumers. In order to be acceptable to consumers, a product must exhibit good cleansing properties, must exhibit good lathering characteristics, must be mild to the skin and preferably should provide a moisturizing benefit to the skin. Ideal personal cleansers should gently cleanse the skin or hair, cause little or no irritation, and not leave the skin or hair overly dry after frequent use.

These traditional forms of personal cleansing products have included two types of formulations, oil free cleansers and oil and water emulsions. The oil free cleansers utilize water based surfactants, fatty acid soaps, synthetic isethionates and the like to remove dirt and oil from the skin. However, many of these surfactants, especially fatty acid soaps, have been found to be irritating to the skin. Milder components and water based humectants are used in order to minimize the skin drying and irritation negatives. The oil and water emulsions utilize insoluble skin conditioning oils along with the water based cleansing systems. The products are formulated to balance the cleansing benefits of the water phase and the conditioning benefits of the oils, which are deposited on the skin. However, it is known that the emulsification of oils in water cleaners negatively impacts the lathering and cleansing properties of the products.

Recently, cosmetics manufacturers have introduced silicone based make-ups, especially lipsticks, which resist smear and rub-off. However, as products are designed to resist removal, they by their nature are more difficult to wash off. The traditional oil free cleansers and oil and water emulsion cleansers have difficulty removing these new products, without being irritating to the skin. A need need clearly exists to develop a method for cleansing the face and specifically a method for removing make-up from the skin.

It has been surprisingly found in the present invention that personal cleansing products can be formulated with properties designed to soften and remove the silicone in these new make-up products. It has been found that solutions of lathering surfactant and water having a pH of less than 8.3 and having an interfacial tension of less than 3.5 provide improved ability to remove silicone based compounds from the skin without increasing skin irritation. The methods of the present invention are highly efficacious for cleansing the skin of the face, especially for removing silicone based compounds from the face. Without being limited by theory, it is believed that the lower than typical interfacial tension better softens and breaks up the lipid and silicone base of the make-up compound. The lower than typical pH reduces irritation over soaps products. This combination provides the improved make-up removal benefit of the methods of the present invention.

The present invention relates to methods of cleaning lipid and silicone based compounds from a solid substrate.

The present invention also relates to methods of cleaning the skin of the face and methods for removing make-up from the face using compositions in which the pH and interfacial tension have been adjusted to remove silicone based compounds from the skin. The methods provide improved cleansing and make-up removal over traditional cleansing methods of cleaning the face.

This and other objects of this invention will become apparent in light of the following disclosure.

SUMMARY OF THE INVENTION

The present invention relates to a method for removing lipid and silicone based compounds from solid substrates comprising:

applying an effective amount of a cleansing composition comprising:

a) from about 5% to about 74.5% of a lathering surfactant; and b) from about 25% to about 94.9% water;

wherein the pH of the composition is less than about 8.3 and wherein the interfacial tension of the composition with mineral oil is less than to about 3.5.

In another embodiment, the present invention relates to a method for removing lipid and silicone based compounds from human skin comprising:

applying a safe and effective amount of a cleansing composition comprising:

a) from about 7.5% to about 50% of a lathering surfactant; and b) from about 50% to about 92.5% water, wherein the pH of the composition is less than about 8.3 and wherein the interfacial tension of the composition with mineral oil is less than about 3.5.

All percentages and ratios used herein, unless otherwise indicated, are by weight and all measurements made are at 25° C., unless otherwise designated. The invention hereof can comprise, consist of or consist essentially of, the essential as well as optional ingredients and components described therein.

DETAILED DESCRIPTION OF THE INVENTION

I. The Cleansing Compositions

The term "cleansing composition" as used herein means a composition suitable for application to a solid substrate for the purpose of removing dirt, make-up, oil and the like. The cleansing compositions of the present invention comprise the following essential components.

A. Lathering Surfactant

The cleansing compositions of the present invention comprise from about 5% to about 74.5%, preferably from about 7.5% to about 50%, and more preferably from about 10% to about 25%/, based on the weight of the cleansing composition, of a lathering surfactant.

By a "lathering surfactant" it is meant a surfactant, which when combined with water and mechanically agitated generates a foam or lather. Preferably, these surfactants should be mild, which means that these surfactants provide sufficient cleansing or detersive benefits but do not overly dry the skin or hair, and yet meet the lathering criteria described above. A lathering surfactant is further defined herein as a synthetic surfactant or mixture of surfactants which has an equilibrium surface tension of between 15 and 50 dynes/centimeter, more preferably between 20 and 45 dynes/ centimeter as measured at the critical miscelle concentration at 25° C. Some surfactant mixtures can have a surface tension lower than any of its components.

The term "mild" as used herein in reference to the lathering surfactants and products of the present invention means that the products of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing products, are based on a skin barrier destruction test. In this test, the milder the surfactant, the lesser the skin barrier is destroyed. Skin barrier destruction is measured by the relative amount of radio-labeled (tritium labeled) water (3H—$H_2O$) which passes from the test solution through the skin epidermis into the physiological buffer contained in the diffusate chamber. This test is described by T. J. Franz in the *J. Invest. Dermatol.*, 1975, 64, pp.190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

A wide variety of lathering surfactants are useful herein and include those selected from the group consisting of anionic lathering surfactants, nonionic lather surfactants, amphoteric lathering surfactants, and mixtures thereof. Cationic surmounts can also be used as optional components, provided they do not negatively impact the overall lathering characteristics of the required, lathering surfactants.

Anionic Lathering Surfactants

Nonlimiting examples of anionic lathering surfactants useful in the compositions of the present invention are disclosed in McCutcheon's, Detergents and Emulsifiers, North American edition (1986), published by allured Publishing Corporation; McCutcheon's, *Functional Materials*, North American Edition (1992); and U.S. Pat. No. 3,929,678, to Laughlin et al., issued Dec. 30, 1975.

A wide variety of anionic lathering surfactants are useful herein. Nonlimiting examples of anionic lathering surfactants include those selected from the group consisting of sarcosinates, sulfides, isethionates, taurates, phosphates, carboxylates, and mixtures thereof. Amongst the isethionates, the alkoyl isethionates are preferred, and amongst the sulfates, the alkyl and alkyl ether sulfates are preferred. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1—SO_3—M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates, nonlimiting examples of which include sodium lauroyl sarcosinate, sodium cocoyl sarcosinate, and ammonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Other anionic materials include the carboxylates, nonlimiting examples of which include sodium laureth carboxylate, sodium lauroyl carboxylate, sodium cocoyl carboxylate, and ammonium lauroyl carboxylate.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl sarcosinate, sodium laureth carboxylate, and mix thereof.

Especially preferred for use herein is sodium laureth sulfate and sodium laureth carboxylate.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g. $C_{8-30}$ alcohols, with sugars or starches or sugar or starch polymers, i.e., glycosides or polyglycosides. These compounds can be represented by the formula $(S)_nO$—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

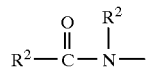

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Other examples of nonionic su tans include amine oxides. Amine oxides correspond to the general formula $R_1R_2R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of $C_8$–$C_{14}$ glucose amides, $C_8$–$C_{14}$ alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition A(1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalknoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-2-hydroxyethyl) carboxymethyl betaine, oleyl dimethyl gamma-carboxypropyl betaine, laryl bis-(2-hydroxypropyl)alpha-carboxyethyl betaine, coco dimethyl sulfopropyl betaine, lauryl dimethyl sulfoethyl betaine, lauryl bis-2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Miritaine CBS from Rhone-Poulenc).

Preferred for use herein are amphoteric surfactants having the following structure:

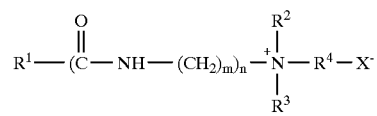

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric swats of the present invention include the following compounds:

Cetyl dimethyl betaine (this material also has the CTFA designation cetyl betaine)

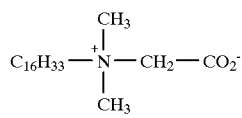

Cocamidopropylbetaine

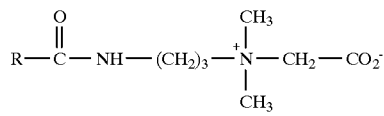

wherein R has from about 9 to about 13 carbon atoms

Cocamidopropyl hydroxy sultaine

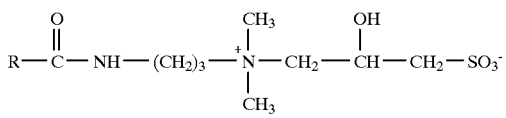

wherein R has from about 9 to about 13 carbon atoms,

Examples of other useful amphoteric surfactants are alkyliminoacetates, and iminodialkanoates and aminoalkanoates n of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirely; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium laureth carboxylate, and mixtures thereof; wherein the nonionic lathering sent is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

B. Water

The compositions of the present invention comprise from about 25% to about 94.9%, preferably from about 35% to about 90%, more preferably from about 40% to about 70% water. The level of water within these ranges which should be employed depends upon the form and rheology of the product desired.

C. pH

The cleansing compositions of the present invention comprise a pH of less than about 8.3, preferably from about 4.0 to about 8.0, and more preferably from about 5.0 to about 7.5. The pH of the composition is measured using standard calibrated pH measuring method ASTM Designation: E 70-90, "Standard Test Method for pH of Aqueous Solutions With the Glass Electrode", hereby incorporated by reference in its entirety.

D. Interfacial Tension

The compositions of the present invention comprise an interfacial tension of less than 3.5, preferably from about 0.5 to about 3.0, and more preferably from about 1.0 to 2.5. The interfacial tension is measured using ASTM Designation: D 971-91, "Standard Test Method for Interfacial Tension of Oil Against Water by the Ring Method", hereby incorporated by reference in its entirety.

E. Optional Ingredients

The compositions of the present invention can comprise a wide range of optional ingredients. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, insoluble skin conditioning oils, insoluble ski conditioning solids, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes solubilizing agents, and suspending agents), suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

Nonlimiting examples of these additional components cited in the *CTFA Cosmetic Ingredient Handbook*, as well as other materials useful herein, include the following: vitamins and derivatives thereof [e.g., vitamin C, Vitamin A (i.e. retinoic acid), retinol, retinoids, panthenol, niacinamide and the like]; sunscreening agents; other silicone materials such as dimethiconol, dimethicone copolyol, and amodimethicone, and the like); anti-oxidants; anti-microbial agents; preservatives; emulsifiers; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., resorcinol sulfur, salicylic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pentaerythritol or an allyl ether of sucrose), crosslinked and noncrosslinked nonionic and cationic polyacrylamides [e.g., Salcare® SC92 which has the CTFA designation polyquaternium 32 (and) mineral oil and Salcare® SC 95 which has the CTFA designation polyquaternium 37 (and) mineral oil (and) PPG-1 trideceth-6, and the nonionic Seppi-Gel polyacrylamides available from Seppic Corp.]; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, to Orr et al., issued Dec. 11, 1990, which is incorporated by reference herein in its entirety.

II. Method of Cleansing

The compositions of the present invention are useful for cleansing lipid and silicone based compounds from solid substrates. The compositions are useful for cleaning such compounds from a wide variety of solid substrates, including but not limited to textile fabrics, human skin and human hair. The compositions of the present invention are especially useful for cleansing of the face and neck areas.

The method for removing lipid and silicone based compounds from solid substrates of the present invention comprises applying a safe and effective amount of the cleansing composition, described hereabove, to the area to be cleansed. "A safe and effective amount" of the cleansing composition will depend upon the needs and usage habits of the individual using the composition. Typical amounts of the present compositions useful for cleansing range from about 0.5 mg($cm^2$ to about 25 mg/$cm^2$ of skin area to be cleansed.

A suitable amount of the cleansing composition can be applied either directly to the solid surface or via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the product can be used alone and wiped-off from the skin using a pad, cotton ball, tissue, or other like device. The cleansing process is typically a two-step process involving application of the product followed either by rinsing of the product with water or wiping without the use of water.

III. Examples of the Cleansing Products

The following examples further describe and demonstrate the cleansing compositions of the embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

EXAMPLES 1–4—BODYWASH PRODUCTS

|  | Ex. 1 | Ex. 2 | Ex. 3 | Ex. 4 |
|---|---|---|---|---|
| Phase A |  |  |  |  |
| Water | 65.72 | 62.72 | 59.72 | 63.72 |
| Disodium EDTA | 0.20 | 0.20 | 0.20 | 0.20 |
| Phase B |  |  |  |  |
| Glycerine | 3.00 | 3.00 | 3.00 | 3.00 |
| Polyquaternium 10 | 0.40 | 0.40 | 0.40 | 0.40 |
| Phase C |  |  |  |  |
| Sodium/Magnesium Laureth-3-3.6 Sulphate | 12.00 | 12.00 | 12.00 | 12.00 |
| Cocamide MEA | 2.80 | 2.80 | 2.80 | 2.80 |
| Sodium Lauoaphoacetate | 6.00 | 6.00 | 6.00 | 6.00 |
| Myristic Acid | 1.60 | 1.60 | 1.60 | 1.60 |
| Magnesium Sulphate Hepta Hydrate | 0.30 | 0.30 | 0.30 | 0.30 |
| Trihydroxystearin | 0.50 | 0.50 | 0.50 | 0.50 |
| PEG-6 Caprylic/Capric Triglycerides | 3.00 | — | — | — |
| Phase D |  |  |  |  |
| Sucrose Polyesters of Cottonate Fatty Acid | — | 3.00 | — | — |
| Sucrose Polyesters of Behenate Fatty Acid | 3.00 | 2.00 | 4.00 | 2.00 |
| Petrolatum | — | 4.00 | 8.00 | — |
| Mineral Oil | — | — | — | 6.00 |
| Phase E |  |  |  |  |
| DMDM Hydantoin | 0.08 | 0.08 | 0.08 | 0.08 |
| Citric Acid | 1.40 | 1.40 | 1.40 | 1.40 |
|  | 100.00 | 100.00 | 100.00 | 100.00 |

All of these compositions have a pH of 8.3 or less and an interfacial tension of 3.5 or less.

Method of manufacture:

1. In a stainless steel vessel combine ingredients in phase A.
2. In a separate vessel combine ingredients in phase B until a homogeneous mixture is formed
3. Add Phase B to phase A.
4. Add phase C ingredients to phase A vessel while heating to 85° C.
5. Cool to 45° C. Add ingredients in phase D and mill for 20 minutes.
6. Continue cooling. When temperature reaches 30° C., add ingredients in phase E.

EXAMPLES 5–8—FACEWASH PRODUCT

|  | Ex. 5 | Ex. 6 | Ex. 7 | Ex. 8 |
|---|---|---|---|---|
| Phase A |  |  |  |  |
| Water | 61.52 | 61.17 | 64.97 | 67.22 |
| Disodium EDTA | 0.10 | 0.10 | 0.20 | 0.20 |
| Citric Acid | — | — | 1.40 | 1.40 |
| Sodium Laureth-3 Sulfate | 3.00 | 3.50 | — | — |
| Sodium Laureth-4 Carboxilate | 3.00 | 3.50 | — | — |
| Laureth-12 | 1.00 | 1.20 | — | — |
| Phase B |  |  |  |  |
| Polyquaternium 10 | — | — | 0.40 | 0.40 |
| Polyquaternium 25 | 0.30 | 0.30 | — | — |
| Glycerine | 3.00 | 3.00 | 3.00 | 3.00 |

-continued

|  | Ex. 5 | Ex. 6 | Ex. 7 | Ex. 8 |
|---|---|---|---|---|
| Phase C |  |  |  |  |
| Sodium Lauroamphoacetate | 6.00 | 6.00 | — | — |
| Lauric Acid | 6.00 | 6.00 | 3.00 | 3.00 |
| Myristic Acid | — | — | 3.00 | 3.00 |
| Magnesium Sulphate Hepta Hydrate | 2.30 | 2.00 | 2.00 | 2.00 |
| Triethanol Amine | 4.00 | 4.00 | 4.00 | 4.00 |
| Sucrose Polyesters of Behenate Fatty Acid | 2.00 | 2.00 | 4.00 | 2.00 |
| Sucrose Polyesters of Cottonate Fatty Acid | 3.00 | 2.00 | — | — |
| Trihydroxystearin | 0.50 | 0.50 | 0.50 | 0.50 |
| Phase D |  |  |  |  |
| Cocamidopropyl Betaine | 2.00 | 3.00 | 1.80 | 1.80 |
| Lauryl dimethyl amine oxide | 1.00 | 1.20 | 1.20 | 1.20 |
| PEG-6 Caprylic/Capric Triglycerides | — | — | — | 2.00 |
| Petrolatum | — | — | 4.00 | — |
| Mineral Oil | — | — | — | 2.00 |
| Dex Panthenol | 1.00 | 0.25 | 0.25 | — |
| Phase E |  |  |  |  |
| DMDM Hydantoin | 0.08 | 0.08 | 0.08 | 0.08 |
| Fragrance | 0.20 | 0.20 | 0.20 | 0.20 |
|  | 100.00 | 100.00 | 100.00 | 100.00 |

All of these compositions have a pH of 8.3 or less and an interfacial tension of 3.5 or less.

Method of manufacture:

1. In a stainless steel vessel combine ingredients in phase A.
2. In a separate vessel combine ingredients in phase B until a homogeneous mixture is formed.
3. Add Phase B to phase A.
4. Add phase C ingredients to phase A vessel while heating to 85° C.
5. Cool to 45° C. Add ingredients in phase D and mill for 20 minutes.
6. Continue cooling. When temperature reaches 30° C., add ingredients in phase E.

EXAMPLE 9—FACEWASH

|  | Ex. 9 |
|---|---|
| Phase A |  |
| Water | 68.05 |
| Disodium EDTA | 0.10 |
| Phase B |  |
| Glycerin | 3.00 |
| Polyquaternium 10 | 0.50 |
| Phase C |  |
| Sodium Lauroyl Sarcossinate | 5.00 |
| Sodium Lauro Amphoacetate | 5.00 |
| Phase D |  |
| Citric Acid | 0.24 |
| DMDM Hydantoin | 0.08 |
| Fragrance | 0.10 |

EXAMPLE 10—FACEWASH PRODUCT

|  | Ex. 10 |
|---|---|
| Phase A |  |
| Water | 67.52 |
| Disodium EDTA | 0.10 |
| Phase B |  |
| Polyquaternium 24 | 0.35 |
| Glycerine | 3.00 |
| Phase C |  |
| Sodium Cocoyl Isethionate | 5.00 |
| Sodium Lauroyl Glutamate | 5.00 |
| Myristic Acid | 3.00 |
| Magnesium Sulphate Hepta Hydrate | 2.40 |
| Triethanol Amine | 3.80 |
| Lauric Acid | 0.50 |
| Trihydroxystearin | 0.50 |
| Phase D |  |
| Cocamidopropyl Betaine | 1.80 |
| Lauryl dimethyl amine oxide | 1.20 |
| Decyl Polyglucose | 1.8 |
| Phase E |  |
| Phenoxyethanol | 0.50 |
| Panthenol | 1.00 |
| DMDM Hydantoin | 0.08 |
| Fragrance | 0.30 |
|  | 100.00 |

This composition have a pH of 8.3 or less and an interfacial tension of 3.5 or less.

Method of manufacture:

1. In a stainless steel vessel combine ingredients in phase A.
2. In a separate vessel combine ingredients in phase B until a homogeneous mixture is formed.
3. Add Phase B to phase A.
4. Add phase C ingredients to phase A vessel while heating to 75° C.
5. Cool to 45° C. Add ingredients in phase D.
6. Continue cooling. When temperature reaches 30° C., add ingredients in phase E.

EXAMPLE 11—MILD FACEWASH

|  | Ex. 11 |
|---|---|
| Phase A |  |
| Water | 68.05 |
| Disodium EDTA | 0.10 |
| Phase B |  |
| Sodium Laureth 3 Sulfate | 5.00 |
| Sodium Laureth 4 Carboxylate | 6.00 |
| Laureth 12 | 1.00 |
| Lauric Acid | 3.00 |
| Triethanolamine | 3.50 |
| Magnesium Sulfate | 2.00 |
| Phase C |  |
| Cocamidopropyl Betaine | 3.00 |
| Lauramine Oxide | 1.00 |
| Decyl Polyglucose | 1.00 |

-continued

| | Ex. 11 |
|---|---|
| Phase D | |
| DMDM Hydantoin | 0.08 |
| Fragrance | 0.20 |

This composition have a pH of 8.3 or less and an interfacial tension of 3.5 or less.

Method of manufacture:
1. In a stainless steel vessel combine ingredients in phase A. Begin mixing.
2. Add ingredients in phase B while heating to 75° C.
3. Heat to 75° C.
4. Cool to 45° C.
5. Add phase C ingredients to phase A vessel.
6. Cool to 30° C.
7. Add ingredients in phase D.

EXAMPLE 12—MILD CLEANSER

| | Ex. 12 |
|---|---|
| Phase A | |
| Water | 65.72 |
| Disodium EDTA | 1.00 |
| Phase B | |
| Glycerine | 3.00 |
| Polyquaternium 10 | 0.20 |
| Phase C | |
| Sodium Laureth Sulfate | 5.00 |
| Sodium Laureth Carboxylate | 5.00 |
| Lauric Acid | 3.00 |
| Triethanolamine | 4.00 |
| Magnesium Sulphate | 2.50 |
| Trihydroxystearin | 1.00 |
| Phase D | |
| Cocamidopropyl Betaine | 1.50 |
| Lauramine Oxide | 2.00 |
| Decyl Polyglucose | 1.20 |
| Phase E | |
| DMDM Hydantoin | 0.08 |
| Fragrance | 0.20 |
| | 100.00 |

This composition have a pH of 8.3 or less and an interfacial tension of 3.5 or less.

Method of manufacture:
1. In a stainless steel vessel combine ingredients in phase A.
2. In a separate vessel combine ingredients in phase B until a homogeneous mixture is formed.
3. Add Phase B to phase A.
4. Add phase C ingredients to phase A vessel while heating to 85° C.
5. Cool to 45° C. Add ingredients in phase D.
6. Continue cooling. When temperature reaches 30° C., add ingredients in phase E.

What is claimed is:

1. A method for removing lipid and silicone based compounds from solid substrates comprising:
   applying an effective amount of a cleansing composition comprising:
   a) from about 5% to about 74.5% of a lathering surfactant; and
   b) from about 25% to about 94.9% water;
   wherein the pH of the composition is less than about 8.3 and
   wherein the interfacial tension of the composition with mineral oil is less than to about 3.5.

2. A method according to claim 1, wherein the lipid and silicone based compound is make-up.

3. A method according to claim 2 wherein the solid substrate is human skin.

4. A method according to claim 4 wherein the human skin is the human facial skin.

5. A method for removing lipid and silicone based compounds from human skin comprising:
   applying a safe and effective amount of a cleansing composition comprising:
   a) from about 7.5% to about 50% of a lathering surfactant; and
   b) from about 50% to about 92.5% water;
   wherein the pH of the composition is less than about 8.3 and
   wherein the interfacial tension of the composition with mineral oil is less than about 3.5.

6. A method for cleansing the skin of the face of a human comprising:
   applying a safe and effective cleansing composition comprising:
   a) from about 5% to about 74.5% of a lathering surfactant; and
   b) from about 25% to about 94.9% water;
   wherein the pH of the composition is less than about 8.3 and
   wherein the interfacial tension of the composition with mineral oil is less than about 3.5.

7. The method of claim 1 further comprising the additional step of rinsing said cleansing composition from said solid substrate with water.

* * * * *

UNITED STATES PATENT AND TRADEMARK OFFICE
CERTIFICATE OF CORRECTION

PATENT NO. : 5,942,238

DATED : August 24, 1999

INVENTOR(S) : David Michael McAtee et al.

It is certified that error appears in the above-identified patent and that said Letters Patent is hereby corrected as shown below:

At column 1, line 63 "soaps" should read --soap-based--.

At column 2, line 32 "water," should read --water;--.

At column 2, line 39 "consist of or" should read --consist of, or--.

At column 2, line 56 "25%/," should read --25%,--.

At column 3, line 27 "surmounts" should read --surfactants--.

At column 3, line 42 "sulfides" should read --sulfates--.

At column 4, line 48 "mix thereof" should read --mixtures thereof--.

At column 5, line 2 "$(S)_n O—R$" should read --$(S)_n$—O—R--.

At column 5, line 21 "$R^2$—$\overset{\overset{O}{\|}}{C}$—$\overset{\overset{R^2}{|}}{N}$—" should read --$R^2$—$\overset{\overset{O}{\|}}{C}$—$\overset{\overset{R^1}{|}}{N}$—--.

At column 5, line 45 "su tans" should read --surfactants--.

At column 6, line 18 "edition A(1986)" should read --edition (1986)--.

At column 6, line 25 "aminoalknoates" should read --aminoalkanoates--.

UNITED STATES PATENT AND TRADEMARK OFFICE
CERTIFICATE OF CORRECTION

PATENT NO. : 5,942,238

DATED : August 24, 1999

INVENTOR(S) : David Michael McAtee et al.

It is certified that error appears in the above-identified patent and that said Letters Patent is hereby corrected as shown below:

At column 6, line 31 "bis-2-hydroxyethyl)" should read --bis-(2-hydroxyethyl)--.

At column 6, line 32 "laryl" should read --lauryl--.

At column 6, line 35 "bis-2-hydroxyethyl)" should read --bis-(2-hydroxyethyl)--.

At column 7, line 5 "amphoteric swats" should read --amphoteric surfactants--.

At column 7, lines 32-33 "aminoalkanoates n of" should read --aminoalkanoates of--.

At column 7, line 35 "is H alkali" should read --is H, alkali--.

At column 7, line 43 "entirely;" should read --entirety;--.

At column 7, line 60 "lathering sent is" should read --lathering surfactant is--.

At column 8, line 42 "ski conditioning" should read --skin conditioning--.

At column 8, line 46 "hydrotropes solubilizing" should read --hydrotropes, solubilizing--.

At column 9, line 2 "resorcinol sulfur" should read --resorcinol, sulfur--.

At column 9, line 26 "Method" should read --Methods--.

At column 9, line 43 "0.5 mg(cm$^2$" should read --0.5 mg/cm$^2$--.

At column 10, line 41 "formed" should read --formed.--.

UNITED STATES PATENT AND TRADEMARK OFFICE
CERTIFICATE OF CORRECTION

PATENT NO. : 5,942,238

DATED : August 24, 1999

INVENTOR(S) : David Michael McAtee et al.

It is certified that error appears in the above-identified patent and that said Letters Patent is hereby corrected as shown below:

At column 11, after Example 9, insert

--This composition has a pH of 8.3 or less and an interfacial tension of 3.5 or less.

Method of manufacture:

1. In a stainless steel vessel combine ingredients in phase A.
2. In a separate vessel combine ingredients in phase B until a homogeneous mixture is formed.
3. Add Phase B to phase A.
4. A phase C ingredients to phase A vessel.
4. Heat to 75°C.
5. Cool to 30°C.
6. Add ingredients in phase D.--.

At column 14, line 26 "claim 4" should read --claim 3--.

Signed and Sealed this

Thirtieth Day of May, 2000

Attest:

Q. TODD DICKINSON

*Attesting Officer*     *Director of Patents and Trademarks*